United States Patent
McCoy

(10) Patent No.: US 7,234,323 B2
(45) Date of Patent: Jun. 26, 2007

(54) RECOVERING NATURAL GAS LIQUIDS FROM LNG USING VACUUM DISTILLATION

(75) Inventor: Michael Monroe McCoy, Sugar Land, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 11/211,278

(22) Filed: Aug. 24, 2005

(65) Prior Publication Data

US 2006/0065015 A1    Mar. 30, 2006

Related U.S. Application Data

(60) Provisional application No. 60/614,664, filed on Sep. 29, 2004.

(51) Int. Cl.
*F25J 3/00* (2006.01)

(52) U.S. Cl. ............................ 62/620; 62/630

(58) Field of Classification Search ............... 62/620, 62/630, 50.2
See application file for complete search history.

(56) References Cited

U.S. PATENT DOCUMENTS

| | | | | |
|---|---|---|---|---|
| 2,952,984 A | * | 9/1960 | Marshall, Jr. ................ 62/622 |
| 3,253,418 A | * | 5/1966 | Harmens ..................... 62/50.3 |
| 3,362,175 A | * | 1/1968 | Burns et al. .................. 62/630 |
| 3,405,530 A | * | 10/1968 | Denahan et al. .............. 62/630 |
| 3,456,032 A | * | 7/1969 | Kniel ........................ 585/650 |
| 3,656,312 A | * | 4/1972 | Streich ........................ 62/630 |
| 4,006,076 A | * | 2/1977 | Christensen et al. ........ 208/211 |
| 4,430,103 A | * | 2/1984 | Gray et al. ................... 62/620 |
| 6,116,050 A | * | 9/2000 | Yao et al. ..................... 62/630 |

\* cited by examiner

*Primary Examiner*—William C. Doerrler
(74) *Attorney, Agent, or Firm*—James W. Ambrosius; Frank C. Turner

(57) ABSTRACT

A process for recovering liquefied $C_3$ compounds from a natural gas stream containing $C_3$ compounds which comprises (a) chilling the natural gas stream under conditions sufficient to liquefy the natural gas, whereby a mixture comprising liquid natural gas (LNG) and liquid $C_3$ compounds is formed; (b) fractionating the mixture comprising liquid natural gas (LNG) and liquid $C_3$ compounds in a separation zone under sub-atmospheric pressure and under conditions predetermined to vaporize a significant portion of the natural gas present while retaining the $C_3$ compounds as a liquid fraction; and (c) recovering separately from the separation zone natural gas and liquid $C_3$ compounds.

21 Claims, 3 Drawing Sheets

RECOVERING NATURAL GAS LIQUIDS FROM LNG USING VACUUM DISTILLATION

CROSS REFERENCE TO RELATED APPLICATIONS

This application claims priority from U.S. Provisional Application No. 60/614,664 filed on Sep. 29, 2004, the entire contents of which are incorporated herein by reference.

FIELD OF THE INVENTION

The present invention is directed to a process for recovering natural gas liquids from liquefied natural gas.

BACKGROUND OF THE INVENTION

Liquefied natural gas (LNG) is principally liquid methane with smaller amounts of $C_2+$ hydrocarbons also present. LNG is prepared by chilling a raw natural gas stream to a temperature and at a pressure sufficient to cause at least a portion of the methane in the raw gas to condense as a liquid. The natural gas stream from which the LNG is made may be recovered from any process which generates light hydrocarbon gases. However, generally the raw natural gas from which LNG is prepared is recovered from a crude oil or gas well.

Raw natural gas is a mixture of various hydrocarbon gases, including $C_2-$ hydrocarbons, and heavier $C_3$ and $C_4$ petroleum gases. "Wet" gas also comprises varying amounts of $C_5+$ hydrocarbons, while "dry" gas comprises little or no $C_5+$ hydrocarbons. As used herein, $C_1$ represents a hydrocarbonaceous compound having one carbon atom per molecule, $C_2$ contains two carbon atoms per molecule, etc. $C_3-C_4$ represents a hydrocarbonaceous material comprising compounds having three carbon atoms per molecule and/or compounds having four carbon atoms per molecule. $C_3+$ compounds represents compounds having three or more carbon atoms per molecule. $C_5+$ represents compounds having five or more carbon atoms per molecule. Methane is a representative example of a $C_1$ compound. Ethane, ethylene, and mixtures thereof are representative examples of $C_2$ compounds. Propane, propene, butane, butenes and mixtures thereof are representative examples of $C_3-C_4$ compounds. Pentanes, pentenes, hexanes, hexenes and comparable higher molecular weight species, and their mixtures, are representative of $C_5+$ compounds.

The process of liquefying natural gas involves chilling the raw natural gas, either at atmospheric or super-atmospheric pressure, until the methane and ethane condense as liquids. On account of their higher molecular weights and lower dew points, any $C_3+$ vapors contained in the raw natural gas condense prior to the condensation of the $C_1$ and $C_2$ compounds, forming a liquid product termed "natural gas liquids" which may be abbreviated as "NGL". Each of the components which condense during the preparation of LNG have important commercial value. $C_1$ and $C_2$ compounds are the major components of LNG and are valuable both as fuel and as feedstock for preparing commercially valuable products. Liquefied petroleum gas (LPG), comprising principally $C_3$ and $C_4$ hydrocarbons, is useful as a refrigerant in the liquefaction process. LPG also may serve as a fuel in the LNG liquefaction process or as transportation or heating fuel. The $C_5+$ condensate recovered from the raw natural gases is valuable as a blending component for fuels, particularly for transportation fuels. Therefore, it is important that the liquefied $C_5+$ condensate and the $C_3-C_4$ LPG be recovered separately from the LNG. The present invention is directed to an efficient process for recovering and storing separate LPG streams in the process of preparing LNG.

As used in this disclosure the words "comprises" or "comprising" are intended as open-ended transitions meaning the inclusion of the named elements, but not necessarily excluding other unnamed elements. The phrases "consists essentially of" or "consisting essentially of" are intended to mean the exclusion of other elements of any essential significance to the composition. The phrases "consisting of" or "consists of" are intended as a transition meaning the exclusion of all but the recited elements with the exception of only minor traces of impurities.

SUMMARY OF THE INVENTION

The present invention relates to a method for separating materials which are included in raw natural gas, particularly the materials which are recovered as natural gas liquids during the preparation of liquefied natural gas. When the process is used primarily to recover $C_3$ compounds from the raw natural gas, the invention may be broadly described as a process for recovering liquefied $C_3$ compounds from a natural gas stream containing $C_3$ compounds which comprises (a) chilling the natural gas stream under conditions sufficient to liquefy the natural gas, whereby a mixture comprising liquid natural gas (LNG) and liquid $C_3$ compounds is formed; (b) fractionating the mixture comprising liquid natural gas (LNG) and liquid $C_3$ compounds in a separation zone under sub-atmospheric pressure and under conditions predetermined to vaporize a significant portion of the natural gas present while retaining the $C_3$ compounds as a liquid fraction; and (c) recovering separately from the separation zone natural gas and liquid $C_3$ compounds. If $C_4+$ compounds are also present additional separations may be used to recover these products as well. In this instance, the additional separation steps may be described as (d) introducing the mixture comprising liquid $C_3-C_4$ compounds into a second separation zone under sub-atmospheric pressure and under conditions predetermined to vaporize a significant portion of the $C_3$ compounds present while retaining the $C_4$ compounds as a liquid fraction; and (e) recovering separately from the second separation zone $C_3$ compounds and liquid $C_4$ compounds.

In the event that the raw natural gas also contains recoverable amounts of $C_5+$ compounds the invention may be described as a process for recovering liquefied $C_3+$ compounds from a natural gas stream containing $C_3$, $C_4$, and $C_5+$ compounds which comprises (a) chilling the natural gas stream under conditions sufficient to liquefy the natural gas, whereby a mixture comprising liquid natural gas (LNG) and liquid $C_3+$ compounds is formed; (b) fractionating the mixture comprising liquid natural gas (LNG) and liquid $C_3+$ compounds in a separation zone under sub-atmospheric pressure and under conditions predetermined to vaporize a significant portion of the natural gas present while retaining the $C_3+$ compounds as a liquid fraction; (c) recovering separately from the separation zone natural gas and a mixture comprising liquid $C_3+$ compounds; (d) introducing the mixture comprising liquid $C_3+$ compounds into a second separation zone under sub-atmospheric pressure and under conditions predetermined to vaporize a significant portion of the $C_3$ and $C_4$ compounds present while retaining the $C_5+$ compounds as a liquid fraction; (e) recovering separately from the second separation zone liquid $C_5+$ compounds and a mixture comprising $C_3$-$C_4$ compounds. The $C_3$ compounds and $C_4$ compounds may be recovered separately by including the additional steps of (f) introducing the mixture comprising the $C_3$-$C_4$ compounds into a third separation zone under sub-atmospheric pressure and under conditions predetermined to vaporize a significant portion of the $C_3$ compounds present while retaining the $C_4$ compounds as a liquid fraction; and (g) recovering separately from the third separation zone $C_3$ compounds and liquid $C_4$ compounds.

Finally, the process may be used as a process for producing a liquefied $C_3$ material and a liquefied $C_4$ material from a mixture comprising $C_3$ and $C_4$ compounds. Accordingly the process may be described as a process for producing liquefied $C_3$ product and liquefied $C_4$ product comprising fractionating a liquid comprising $C_3$ compounds and $C_4$ compounds in a separation zone at pressures under sub-atmospheric pressure and separately recovering at least liquefied $C_3$ product and liquefied $C_4$ product. As will be explained in greater detail below, this embodiment of the process may be used to recover boil off gas from $C_3$ and $C_4$ storage facilities.

DETAILED DESCRIPTION OF THE INVENTION

In the process of the invention, liquefied $C_3$ compounds and liquefied $C_4$ compounds are produced by separating a natural gas liquid at sub-atmospheric pressure in a series of fractionation zones. As used herein, separation, distillation or fractionation at sub-atmospheric pressure means distillation at a pressure less than the ambient pressure, and typically less than 15 psia (absolute pressure in pounds per square inch). It may also be termed "vacuum" distillation. Conventional methods for making these separations include fractionation at elevated temperatures and under pressure. In contrast, in the present process the distillations are performed at low temperatures and at pressures below 15 psia (i.e., at sub-atmospheric pressure), and most preferably at pressures below 12 psia. In the practice of the invention, costs involved in heating and pressurizing the light hydrocarbon streams are significantly reduced. In addition, LPG products, including liquefied propane and liquefied butane, can be recovered from the fractionation process without requiring significant additional condensing and pressurization beyond that required for pumping the fluids through the liquefaction process.

In one embodiment of the invention in which $C_3$, $C_4$, and $C_5+$ compounds are separately recovered from wet raw natural gas, the process utilizes three separations zones generally referred to in the art as a deethanizer, debutanizer, and depropanizer, respectively. The deethanizer which is intended for the separation of $C_2-$ compounds from $C_3+$ compounds is generally operated at a pressure of less than 12 psia and at a bottoms temperature within the range of from about 0° F. (about –17.8° C.) to about 200° F. (about 93.3° C.). Preferably, the bottoms temperature of the deethanizer is maintained within the range of from about 20° F. (about –6.67° C.) to about 150° F. (about 65.6° C.). The debutanizer which is intended for the recovery of $C_3$ compounds from $C_4+$ compounds is generally operated at a pressure of less than 12 psia and at a bottoms temperature within the range of from about 20° F. (about –6.67° C.) to about 250° F. (about 121° C.). Preferably, the bottoms temperature of the debutanizer is maintained within the range of from about 40° F. (about 4.44) to about 150° F. (about 65.6° C.). The depropanizer which is intended for the recovery of $C_4$ compounds from $C_5+$ compounds is generally operated at a pressure of less than 12 psia and at a bottoms temperature within the range of from about –75° F. (about –59.4° C.) to about 75° F. (about 23.9° C.). Preferably, the bottoms temperature of the depropanizer is maintained within the range of from about –50° F. (about –45.6° C.) to about 50° F. (about 10° C.).

Figure 1:
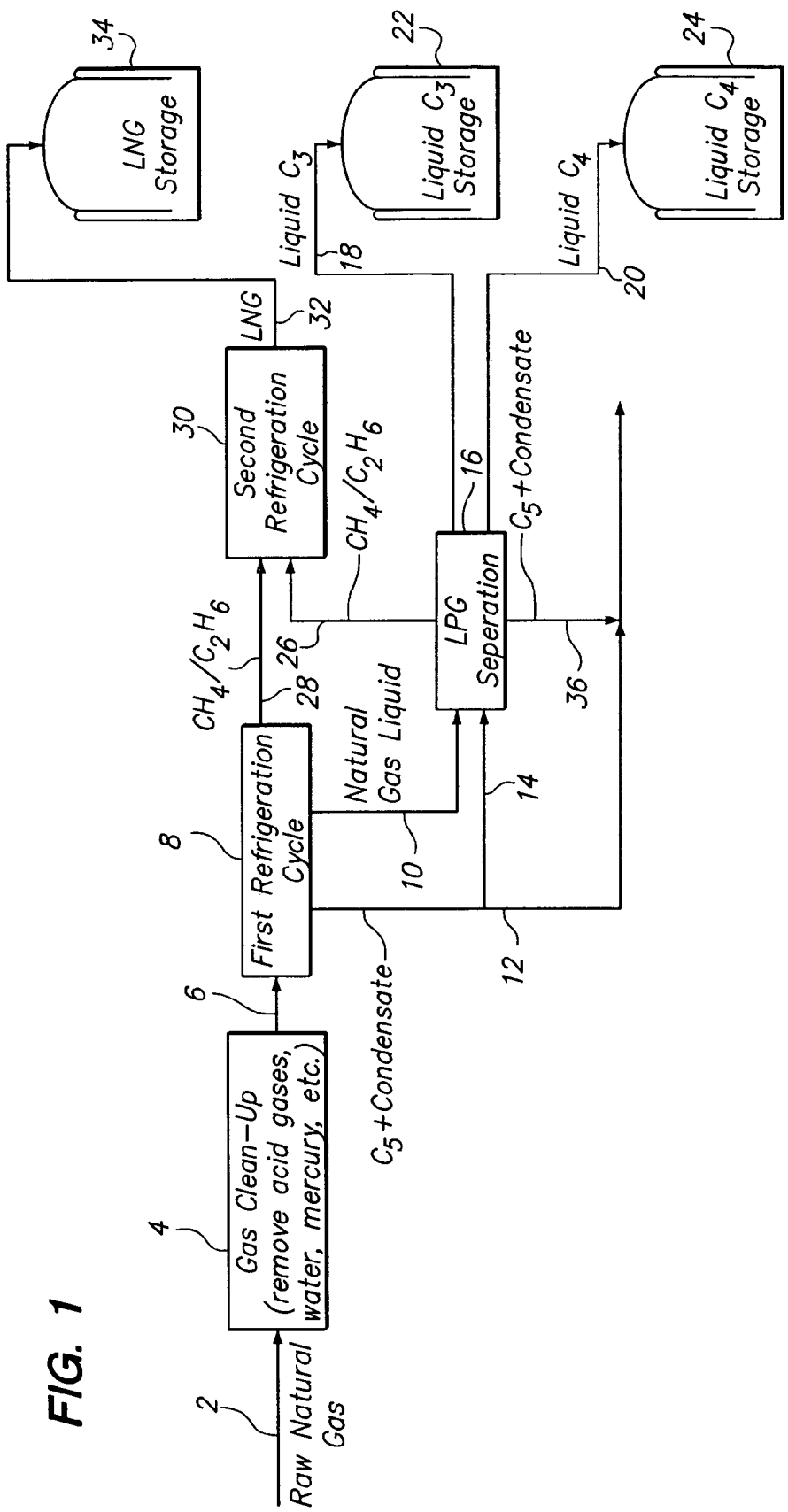
FIG. 1 represents a flow diagram illustrating a typical scheme for recovering NGL from raw natural gas.

The present invention will be more clearly understood by reference to the drawings. FIG. 1 represents a typical process scheme for recovering natural gas liquids (NGL) from raw natural gas. In FIG. 1, the raw natural gas stream (2) from which LNG is made is recovered from a production well, either alone or in combination with heavier crude products. The raw natural gas stream typically comprises methane, $C_2$-$C_4$ hydrocarbons, and generally lesser amounts of $C_5+$ condensate. The raw natural gas stream may contain $C_5+$ condensate at a concentration within a wide range, and, if the $C_5+$ hydrocarbons in the natural gas stream are present in recoverable amounts, the gas is referred to as "wet" natural gas. Wet natural gas will typically contain up to 20% by volume $C_5+$ condensate (e.g., 0.5%-20%). "Dry" natural gas will contain virtually no $C_5+$ condensate. The stream may also contain contaminants such as water, carbon dioxide, hydrogen sulfide, nitrogen, dirt, iron sulfide, wax, crude oil, diamondoids, mercury and the like. These contaminants are generally undesirable in the liquefied LNG and NGL products. Contaminants which condense as separate liquid or solid phases during chilling cause problems during the refrigeration steps, and are necessarily removed. Acid contaminants which may lead to corrosion of the refrigeration materials are also desirably removed. These contaminants may be removed by conventional means (4) which are well known in the art. After the natural gas stream is cleaned to remove contaminants, it is sent by line 6 to be chilled in a $1^{st}$ refrigeration zone (8), which comprises one or more refrigeration cycles. Example coolants used in $1^{st}$ refrigeration zone (8) include LNG, LPG or mixtures thereof. The chilling process produces a natural gas liquid stream (10) and often a separate $C_5+$ condensate stream (12).

As shown in FIG. 1, the $C_5+$ condensate stream (12) removed from the $1^{st}$ refrigeration cycle may optionally be sent by line 14 to the LPG separation zone (16) for removing any $C_4-$ components (i.e., $C_4$ and lighter) which are contained in it.

Natural gas liquids (10) from the $1^{st}$ refrigeration zone (8) are also passed to an LPG separation zone (16) for the isolation and separate recovery of liquid $C_3$ compounds (18) and liquid $C_4$ compounds (20). The $C_3$ and $C_4$ hydrocarbon products are sent to storage vessels (22) and (24), respectively. The $C_3$ compounds in stream (18) and in tank (22) comprises liquid $C_3$ hydrocarbons which are primarily propane. There will generally be amounts of both $C_3H_8$ and $C_3H_6$ hydrocarbons in the liquid $C_3$ product, the ratio of the two species ranging from 100% $C_3H_8$ to 100% $C_3H_6$. However, $C_3H_8$ generally will be the predominant hydrocarbon. There may also be small amounts of contaminants in the liquid $C_3$ product, including some $C_2-$ materials and some C$_4$+ materials. The same is true for the C$_4$ product stream (20) which is stored in tank (24). There will generally be amounts of both C$_4$H$_{10}$ and C$_4$H$_8$ hydrocarbons in the liquid C$_4$ product, the ratio of the two species ranging from 100% C$_4$H$_{10}$ to 100% C$_4$H$_8$. Generally, C$_4$H$_{10}$ will be the predominant hydrocarbon. There may also be small amounts of contaminants in the liquid C$_4$ product, including some C$_3$– materials and some C$_5$+ materials. A fuel gas stream (26) which is also recovered from the LPG separation zone (16) is combined with natural gas stream (28) from 1$^{st}$ refrigeration zone (8) for additional cooling in the 2$^{nd}$ refrigeration zone (30). LNG is recovered as a liquid stream (32) from the 2$^{nd}$ refrigeration zone for storage in storage vessel 34. In one embodiment of the process, LNG stored in 34 and C$_3$ product and C$_4$ product respectively stored in 22 and 24 are maintained at nominally atmospheric pressure, the actual pressure being slightly higher than ambient pressure to account for the vapors which are being generated by the evaporating liquids and which are being vented from the storage vessels. The two C$_5$+ condensate streams (12) and (36), if present, may be combined or used separately in downstream processing, as fuel, as a petrochemical feedstock, and the like.

The present invention is concerned primarily with the design and operation of the LPG separation zone (16) shown in FIG. 1. In a typical conventional method of recovering the propane and butane (LPG) and the crude condensate (a C$_5$+ stream of hydrocarbons) from an LNG facility a series of fractionation columns are employed which have operating pressures in the 120 psig to 230 psig range and operating temperatures in the 150° F. (65.6° C.) to 330° F. range (166° C.), depending on the column. In an LNG facility, operating at these temperatures and pressures requires a large amount of energy to heat the LPG and condensate stream from less than –100° F. (–18.6° C.) to the 200° F. (93.3° C.) range. Furthermore, LNG plants, unless they have a heat recovery system, do not produce a sufficiently hot stream that could be used as a heating medium in the column reboilers and, therefore, it is necessary to install a special process heater to provide the heat input for the reboilers on the columns. Also, if the project specifics mandate atmospheric storage, the LPG streams must be cooled back down to about –50° F. (–45.6° C.) for storage which again requires a large amount of energy. Table 1 lists typical operating conditions for the fractionation columns in a conventional LPG separation section.

TABLE 1

Typical Operating Conditions for Separation of Light Petroleum Fractions in a Conventional LPG Separation Process

| | Temp. ° F. | Press. psig |
|---|---|---|
| Deethanizer | | |
| Overhead | 115° F. | 200 psig |
| Bottoms | 290° F. | |
| Debutanizer | | |
| Overhead | 150° F. | 120 psig |
| Bottoms | 330° F. | |
| Depropanizer | | |
| Overhead | 120° F. | 230 psig |
| Bottoms | 220° F. | |

LPG separations under the operating conditions shown in Table 1 are suitable for a conventional refinery system, in which sufficient high temperature streams are available for heating the reboiler exchangers to the high bottoms temperatures typical of the conventional process by using steam or other readily available streams as the heating medium.

Figure 2:
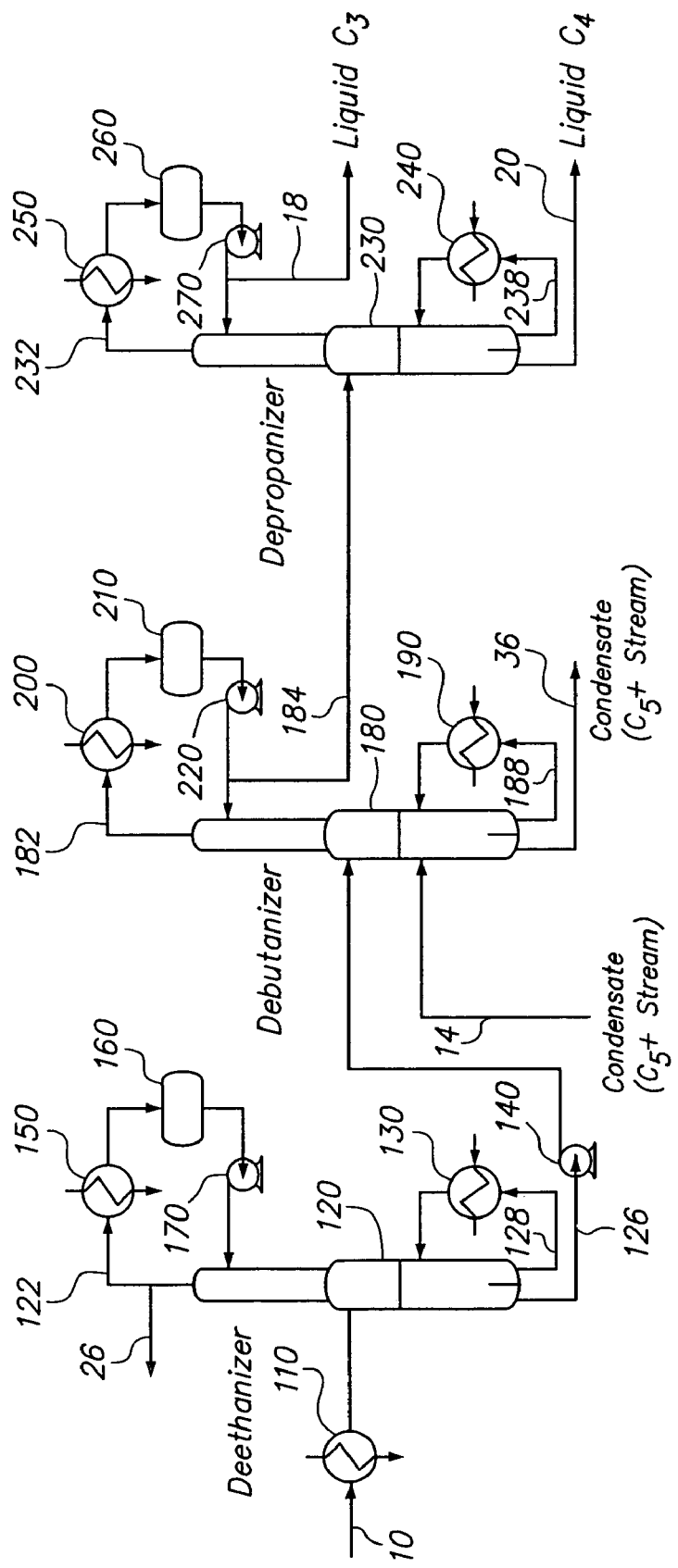
FIG. 2 is a schematic diagram of the LPG recovery section shown in FIG. 1 which illustrates one embodiment of the present invention.

FIG. 2 illustrates one embodiment of the process of the invention, showing the separation and recovery of liquefied C$_3$ product and liquefied C$_4$ product as separate streams in a multiple fractionation process shown generally in FIG. 1 as LPG separation zone (16). Natural gas liquid (10) from the 1$^{st}$ refrigeration zone is prepared in heat exchanger (110) prior to separation in 1$^{st}$ fractionation zone (120). Depending on the temperature of the natural gas liquid (10), this stream may be either cooled or heated in heat exchanger (110). Normally, heating will be required. Methods of heating fluid streams are well-known in the art and should not require further explanation here. The natural gas liquid (10) is fractionated in the 1$^{st}$ fractionation zone (120) to remove light materials, primarily methane and ethane. The fractionation is conducted at sub-atmospheric pressure and at a temperature selected to maintain an acceptable separation efficiency. Methods for maintaining a vacuum during distillation are well known, and include, for example, use of an eductor or a vacuum pump. Table 2 broadly lists operating conditions which are useful in the present process, and includes two exemplary cases, a lower temperature/lower pressure case and a higher temperature/relatively higher pressure case. Typical operating conditions for each fractionation column are shown in Table 3. In all cases, fractionation pressure in each fractionation zone is maintained in the sub-atmospheric range.

To maintain a suitable temperature in the bottom of 1$^{st}$ fractionation zone (120), reboiler (130) serves to heat the recycle liquid (128). Such a reboiler is easily designed by one skilled in the art, and a detailed description of this heater is not required here. Any suitable heating medium, e.g. water, may be used, so long as the temperature of the heating medium is higher than the desired temperature of the recycle liquid.

A portion of overhead vapor product (122) is cooled and condensed in exchanger (150). The cooled and at least partially liquefied stream is stored in reflux drum (160) and then returned to the column via pump (170). The cooling medium used to cool the reflux stream (122) will be any suitable liquid which is at a lower temperature than the reflux fluid. When the present process is included within a process for preparing LNG from a raw natural gas stream, the cooling medium will generally be selected from one of LNG, LPG or a mixture thereof. Liquid methane (or LNG) is particularly suited for this use, both because of its low temperature, and because the overall LNG process is ideally suited for re-condensing a methane vapor which is generated when liquefied methane is used in cooling exchanger (150). Overhead product (26) from the 1$^{st}$ fractionation zone (120), also termed a deethanizer, is recovered as fuel gas or is passed to the 2$^{nd}$ refrigeration zone (30), which is illustrated in FIG. 1, for conversion to LNG.

Bottoms product from fractionation zone (120) is collected in line 126 and sent to downstream processing for removal of any remaining C$_5$+ condensate and for separation of individual liquid propane and liquid butane streams.

In the exemplary embodiment of FIG. 2, stream (126) is passed via pump (140) to the 2$^{nd}$ fractionation zone (180), also referred to as a debutanizer, for removing any C$_5$+ condensate 36. Fractionation zone (180) is also maintained at sub-atmospheric pressure. Recycle liquid (188) at the bottom of fractionation zone (180) is maintained at a temperature selected to achieve a desirable separation of the C$_5$+ condensate collected in line 36. Any suitable heating medium, e.g. water, may be used to provide heat in the reboiler (190). Overhead vapor product (182) from fractionation zone (180) is cooled sufficiently in condenser (200) to condense at least a portion of the stream into the liquid phase. Example coolants include LNG, LPG or mixtures thereof. The cooled stream is collected in reflux drum (210) and then passed via pump (220) back to the column as reflux. A portion of the liquid overhead product is removed as stream (184) from the reflux stream and is passed to $3^{rd}$ fractionation zone (230) for separation of a liquid propane stream (18) and a liquid butane stream (20). To facilitate the separation, a portion of the liquid at the bottom of fractionation zone (230) is removed as recycle liquid (238), heated in heater (240) and returned as recycle liquid to the column. As in the other columns, heater (240) may include a suitable heating medium, such as natural gas liquid stream (10), an LPG stream or the exhaust from a fin fan exchanger.

In the particular embodiment shown in FIG. 2, liquid butane (20) is removed as a liquid bottoms product from fractionation zone (230). Liquid propane (18) is removed as an overhead product from the reflux loop of fractionation zone (230). Overhead vapor product (232) is cooled and at least partially condensed in condenser (250), collected in reflux drum (260) and returned as liquid reflux to the column. A portion of the reflux stream is removed as liquid propane (18). Cooling of the overhead stream in condenser (250) generally employs a liquid which is at a temperature lower than the desired temperature of the reflux. Example coolants include LNG, LPG or a mixture thereof.

It will be seen that in the embodiment illustrated in FIG. 2 that the $C_5+$ condensate is first removed and recovered from $2^{nd}$ fractionation zone (180) (also termed a debutanizer), and an overhead stream (184) is passed from the $2^{nd}$ fractionation zone to a $3^{rd}$ fractionation zone (230), also termed a depropanizer, from which separate liquefied $C_3$ material (18) and liquefied $C_4$ material (20) are recovered. In the embodiment of the invention shown in FIG. 2, therefore, the process comprises multiple fractionation zones, including a deethanizer, a debutanizer and a depropanizer in that order. In a separate embodiment of the invention, the order may be altered, such that the deethanizer is followed by a depropanizer followed by a debutanizer. When the depropanizer precedes the debutanizer, a liquid propane product is recovered by fractionation of the bottoms stream (126) in a depropanizer, and a following fractionation step separates the liquid bottoms product from the depropanizer into at least a liquid butane stream and a bottoms $C_5+$ condensate stream in a debutanizer. The order of separations of the depropanizer and debutanizer depends, at least in part, on the relative amounts of propane, butane and $C_5+$ condensate in the natural gas liquid. Minimum energy requirements are the primary objective in selecting the order of separations.

TABLE 2

Operating Ranges for Fractionation Columns Shown in FIG. 2

| | Broad Range | | Low Pressure | | High Pressure | |
|---|---|---|---|---|---|---|
| | Temp. ° F. | Press. psia | Temp. ° F. | Press. psia | Temp. ° F. | Press. psia |
| Deethanizer (120) | | | | | | |
| Overhead (122) | −150 to 0 | <1 atm | −100 | 3 | −50 | 8 |
| Bottoms (126) | 0 to 200 | | 60 | | 120 | |
| Debutanizer (180) | | | | | | |
| Overhead (182) | −100 to 50 | <1 atm | −50 | 3 | 0 | 8 |
| Bottoms (186) | 20 to 250 | | 70 | | 130 | |
| Depropanizer (230) | | | | | | |
| Overhead (232) | −150 to 0 | <1 atm | −100 | 3 | −50 | 12 |
| Bottoms (236) | −75 to 75 | | 130 | | 10 | |

Typical operations conditions for each fractionation column shown in FIG. 2 are shown in Table 3, below. Temperatures are shown for both a high and low pressure case. One skilled in the art will understand that the pressure within a particular column will vary slightly between the bottom and the top of the column. The listed pressure in Table 3 is the nominal pressure, representing, for example, the pressure at the feed inlet to the column. Pressures at various points along the column will vary from the nominal value depending on such factors as, for example, the size of the column, the type and number of internals in the column, the throughput through the column, and the magnitude of the nominal pressure. These features are part of standard fractionation column design, and the methods for accounting for these features are well known in the art.

TABLE 3

Typical Nominal Operating Conditions for the Fractionation Columns Shown in FIG. 2

| | Low Pressure | | High Pressure | |
|---|---|---|---|---|
| | Temp ° F. | Press. Psia | Temp ° F. | Press. Psia |
| Deethanizer (120) | 60 | 3 | 120 | 8 |
| Debutanizer (180) | −50 | 3 | 0 | 8 |
| Depropanizer (230) | −100 | 3 | −50 | 12 |

LPG may be maintained stored at essentially atmospheric pressure as a liquid in a storage tank by continuously vaporizing a small amount of the cold liquid in the tank containing the LPG. This boil off gas is usually recovered and blended into the fuel gas stream or recondensed and returned to the storage tank. Because of its value in the system, it is desirable to recondense this boil off gas and return it to the storage tanks. One method for recondensing the boil off gas is illustrated in the separate embodiment shown in FIG. 3.

Figure 3:
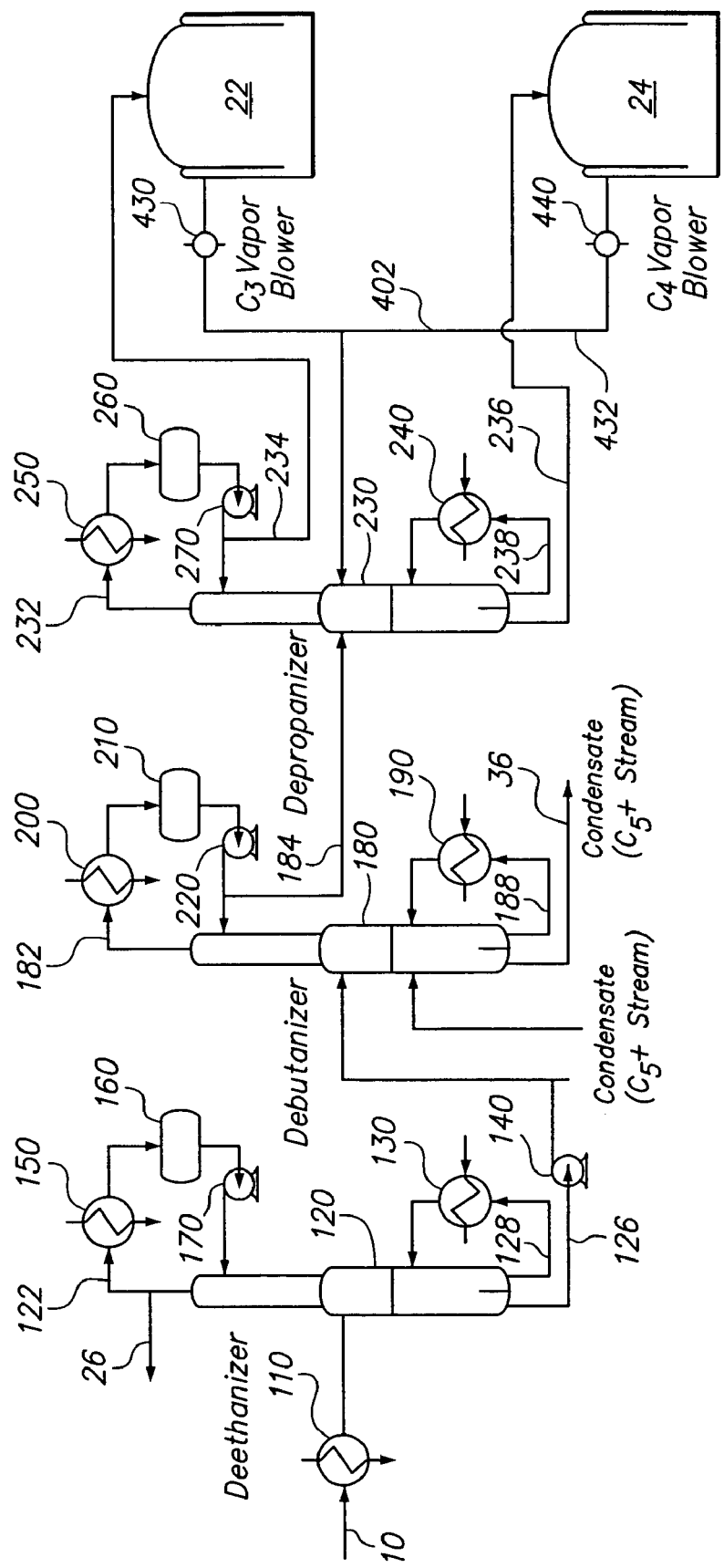
FIG. 3 is a schematic diagram illustrating an embodiment of the invention in which boil off gas from the $C_3$ and $C_4$ storage facilities is recovered.

The embodiment shown in FIG. 3 is essentially the same as the scheme illustrated in FIG. 2 except storage tanks (22) and (24) for holding the $C_3$ and $C_4$ products, respectively, have been added to illustrate the boil off gas recovery system. According to this embodiment, the boil off gas from liquid $C_3$ product storage tank (22) is vented through line 402; likewise the boil off gas from liquid $C_4$ product storage tank (24) is vented through line 432. In the embodiment illustrated in FIG. 3, the two vented vapor streams (402) and (432) are pressurized slightly through blowers (430) and (440), respectively, and then combined for passage to the $3^{rd}$ fractionation zone (230) also referred to as the depropanizer. The boil off gases are then recovered as liquid products from the fractionation zone and returned to the respective tanks (22) and (24).

FIG. 3 illustrates the combination of the $C_3$ boil off gas (402) being combined with the $C_4$ boil off gas (432) and the combination passed to distillation for recover of separate LPG streams. Alternatively, the $C_3$ boil off gas (402) and the $C_4$ boil off gas (432) may be passed separately to the depropanizer. In this embodiment separate liquid $C_3$ products and liquid $C_4$ products are recovered from the fractionation zone as before.

What is claimed is:

1. A process for recovering liquefied $C_3$ compounds from a natural gas stream containing $C_3$ compounds which comprises:
   (a) chilling the natural gas stream under conditions sufficient to liquefy the natural gas, whereby a mixture comprising liquid natural gas (LNG) and liquid $C_3$ compounds is formed;
   (b) fractionating the mixture comprising liquid natural gas (LNG) and liquid $C_3$ compounds in a separation zone under sub-atmospheric pressure and under conditions predetermined to vaporize a significant portion of the natural gas present while retaining the $C_3$ compounds as a liquid fraction; and
   (c) recovering separately from the separation zone natural gas and liquid $C_3$ compounds.

2. The process of claim 1 wherein the separation zone is maintained at a pressure of less than 12 psia and at a bottoms temperature within the range of from about 0° F. to about 200° F.

3. The process of claim 2 wherein the bottoms temperature in the separation zone is maintained at a temperature within the range from about 20° F. to about 150° F.

4. The process of claim 1 wherein the natural gas stream also contains $C_4$ compounds and a mixture comprising liquid $C_3$-$C_4$ compounds are recovered from the separation zone.

5. The process of claim 4 including the additional steps of:
   (d) introducing the mixture comprising liquid $C_3$-$C_4$ compounds into a second separation zone under sub-atmospheric pressure and under conditions predetermined to vaporize a significant portion of the $C_3$ compounds present while retaining the $C_4$ compounds as a liquid fraction; and
   (e) recovering separately from the second separation zone $C_3$ compounds and liquid $C_4$ compounds.

6. The process of claim 5 wherein the second separation zone is maintained at a pressure of less than 12 psia and at a bottoms temperature within the range of from about 20° F. to about 250° F.

7. The process of claim 6 wherein bottoms temperature in the second separation zone is maintained within the range of from about 40° F. to about 150° F.

8. The process of claim 5 wherein the natural gas stream also contains $C_5$+ compounds and a mixture comprising liquid $C_4$ and $C_5$+ compounds are recovered from the second separation zone.

9. The process of claim 8 including the additional steps of:
   (f) introducing the mixture comprising liquid $C_4$ and $C_5$+ compounds into a third separation zone under sub-atmospheric pressure and under conditions predetermined to vaporize a significant portion of the $C_4$ compounds present while retaining the $C_5$+ compounds as a liquid fraction; and
   (g) recovering separately from the third separation zone $C_4$ and $C_5$+ compounds.

10. The process of claim 9 wherein the third separation zone is maintained at a pressure of less than 12 psia and at a bottoms temperature within the range of from about −75° F. to about 75° F.

11. The process of claim 10 wherein the bottoms temperature in the third separation zone is maintained within the range of from about −50° F. to about 50° F.

12. A process for recovering liquefied $C_3$+ compounds from a natural gas stream containing $C_3$, $C_4$, and $C_5$+ compounds which comprises:
   (a) chilling the natural gas stream under conditions sufficient to liquefy the natural gas, whereby a mixture comprising liquid natural gas (LNG) and liquid $C_3$+ compounds is formed;
   (b) fractionating the mixture comprising liquid natural gas (LNG) and liquid $C_3$+ compounds in a separation zone under sub-atmospheric pressure and under conditions predetermined to vaporize a significant portion of the natural gas present while retaining the $C_3$+ compounds as a liquid fraction;
   (c) recovering separately from the separation zone natural gas and a mixture comprising liquid $C_3$+ compounds;
   (d) introducing the mixture comprising liquid $C_3$+ compounds into a second separation zone under sub-atmospheric pressure and under conditions predetermined to vaporize a significant portion of the $C_3$ and $C_4$ compounds present while retaining the $C_5$+ compounds as a liquid fraction;
   (e) recovering separately from the second separation zone liquid $C_5$+ compounds and a mixture comprising $C_3$-$C_4$ compounds.

13. The process of claim 12 wherein the second separation zone is maintained at a pressure of less than 12 psia and at a bottoms temperature within the range of from about −75° F. to about 75° F.

14. The process of claim 13 wherein the bottoms temperature in the second separation zone is maintained within the range of from about −50° F. to about 50° F.

15. The process of claim 12 including the additional steps of:
   (f) introducing the mixture comprising the $C_3$-$C_4$ compounds into a third separation zone under sub-atmospheric pressure and under conditions predetermined to vaporize a significant portion of the $C_3$ compounds present while retaining the $C_4$ compounds as a liquid fraction; and
   (g) recovering separately from the third separation zone $C_3$ compounds and liquid $C_4$ compounds.

16. The process of claim 15 wherein the third separation zone is maintained at a pressure of less than 12 psia and at a bottoms temperature within the range of from about 20° F. to about 250° F.

17. The process of claim 16 wherein bottoms temperature in the third separation zone is maintained within the range of from about 40° F. to about 150° F.

18. A process for producing liquefied $C_3$ product and liquefied $C_4$ product comprising fractionating a liquid comprising $C_3$ compounds and $C_4$ compounds in a separation zone at pressures maintained at sub-atmospheric pressure and separately recovering at least liquefied $C_3$ product and liquefied $C_4$ product.

19. The process of claim 18 wherein the pressure in the separation zone is maintained below 12 psia.

20. The process of claim 18 wherein boil off gas from a $C_3$ product storage facility is added to the separation zone and recovered as part of the liquefied $C_3$ product.

21. The process of claim 18 wherein boil off gas from a $C_4$ product storage facility is added to the separation zone and recovered as part of the liquefied $C_4$ product.

* * * * *